United States Patent

Hanson et al.

[11] Patent Number: 5,271,892
[45] Date of Patent: Dec. 21, 1993

[54] SYSTEM FOR DISINFECTING AND DISPOSING MEDICAL SHARPS

[75] Inventors: Leila Hanson; Joseph J. Hanson, both of Brookfield, Wis.

[73] Assignee: AvanTech Resource Center, Broofield, Wis.

[21] Appl. No.: 870,943

[22] Filed: Apr. 20, 1992

Related U.S. Application Data

[63] Continuation-in-part of Ser. No. 836,629, Feb. 13, 1992.

[51] Int. Cl.⁵ ............................................ A61L 2/18
[52] U.S. Cl. ........................................ 422/25; 422/28; 422/292; 422/300; 206/366; 206/370; 493/963
[58] Field of Search ............ 422/25, 300, 301, 28, 422/32, 292; 222/541–543; 493/963; 206/370, 366

[56] References Cited

U.S. PATENT DOCUMENTS

| | | | |
|---|---|---|---|
| Re. 29,850 | 11/1978 | Labarre | 222/541 |
| 2,475,052 | 7/1949 | Rosen | 493/963 X |
| 3,563,425 | 1/1969 | Clark | 222/478 |
| 3,774,822 | 11/1973 | Hazard | 222/541 |
| 3,811,604 | 5/1974 | Perry | 222/429 |
| 3,828,973 | 8/1974 | Birrell | 222/1 |
| 3,903,335 | 4/1973 | Jones | 427/361 |
| 3,937,323 | 2/1976 | Sagi et al. | 354/317 |
| 3,944,096 | 3/1976 | Eldridge, Jr. | 206/350 |
| 3,990,615 | 11/1976 | Kerwin et al. | 222/541 |
| 4,076,882 | 2/1978 | Fenster et al. | 428/215 |
| 4,080,615 | 3/1978 | Stella | 354/317 |
| 4,182,448 | 1/1980 | Huck et al. | 206/380 |
| 4,218,155 | 8/1980 | Weider | 401/132 |
| 4,321,999 | 3/1982 | Higgins | 206/370 |
| 4,637,513 | 1/1987 | Eldrige, Jr. | 206/370 |
| 4,674,676 | 6/1987 | Sandel et al. | 229/142 |
| 4,754,898 | 5/1988 | Britt et al. | 222/487 |
| 4,807,785 | 2/1989 | Pritchett | 222/442 |
| 4,875,896 | 10/1989 | Kurtz | 604/187 |
| 4,895,275 | 1/1990 | Quinn et al. | 222/81 |
| 4,900,500 | 2/1990 | Honeycutt | 264/263 |
| 4,921,491 | 5/1990 | Champ | 604/199 |

FOREIGN PATENT DOCUMENTS

1355439 9/1971 United Kingdom.
1365769 3/1972 United Kingdom.
2078677 6/1981 United Kingdom.

*Primary Examiner*—Robert J. Warden
*Assistant Examiner*—E. Leigh Dawson
*Attorney, Agent, or Firm*—Reinhart, Boerner, Van Deuren, Norris & Rieselbach

[57] ABSTRACT

A portable disinfecting and disposal device for medical waste. The device top portion includes a chemically filled packet which is sealed during ongoing use for attachment of medical waste to the device. Alternatively, the top portion includes a chemically filled container with access openings which is sealed during ongoing use for attachment of medical waste. The top portion is unsealed to release disinfecting chemical onto collected medical waste by removing a peelable cover. The cover can be removed in whole or part by a peel tab or strings attached to the cover.

19 Claims, 3 Drawing Sheets

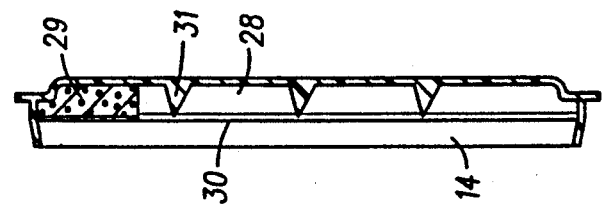
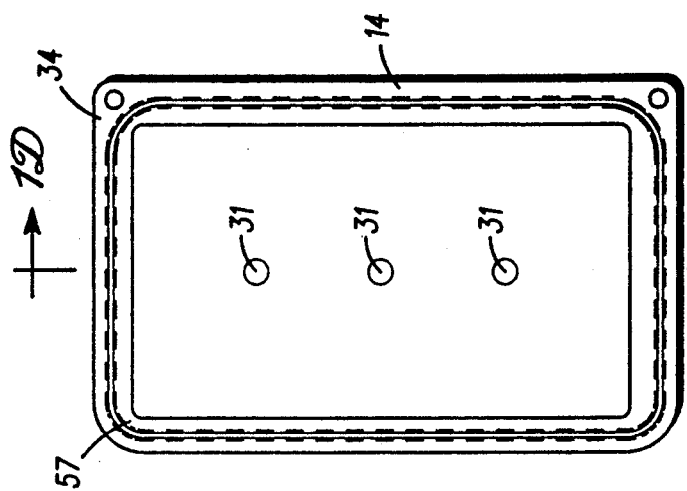
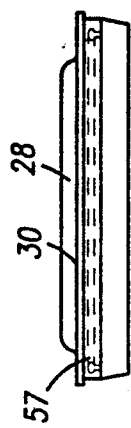
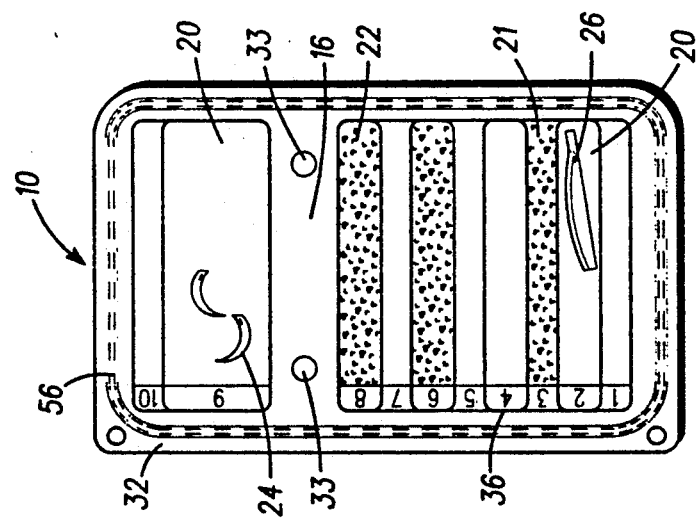
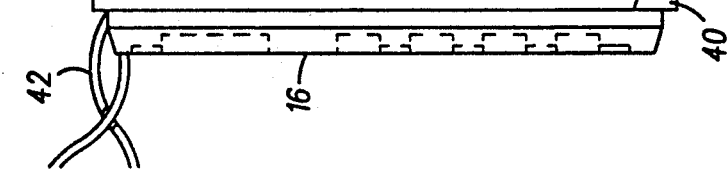

SYSTEM FOR DISINFECTING AND DISPOSING MEDICAL SHARPS

This is a continuation-in-part of copending application Ser. No. 07/836,629, filed on Feb. 13, 1992.

The present invention is concerned generally with an improved method and device for the safe disposal of various surgical and other medical implements which are contaminated with biological media and other contaminated hazardous medical materials. More particularly, the invention is concerned with a new method and device for reliably insuring safe disposal of contaminated medical sharps while also disinfecting the contaminated sharps in the device at the immediate medical site where the medical procedures are taking place.

Devices for disposal of medical waste materials, including sharps used in surgical procedures, are commonly used in medical facilities. Such medical waste is considered hazardous waste and requires, by law (for example, OSHA regulations, state laws and regulations), the use of special handling and disposal procedures which are costly and inefficient. These laws however do little to alleviate a number of serious hazards to the environment and to the handlers of such waste materials, particularly at the site of the generation of the medical waste. Conventional disposer units do not normally allow for affirmatively neutralizing the biological hazard at the immediate medical site. Such hazards as contaminating bacteria and viruses remain intact and active in prior art devices after the waste materials are placed in the disposal device. Such devices therefore continue to harbor contaminated waste as the device is transported from the site of the medical procedure through the disposal system used by the medical institution and continuing through the external waste hauling system, if the medical institution does not have its own decontamination equipment. Only upon reaching a remote site is the biological contamination finally neutralized. The only currently available reasonable alternatives are on-site systems for large medical institutions which utilize complex, mass decontamination machinery for processing medical waste.

In addition, a number of current disposer devices do not affirmatively lock when closed, resulting in disposer containers being accidentally or intentionally reopened thereby exposing medical and waste disposal personnel to dangerous biological contaminants.

A number of currently used disposal devices are also easily penetrable, and ones which are made of heavy-gauge plastic have difficult to seal openings or the seal openings are easily defeated.

Further, a number of prior art disposal devices have low friction outer surfaces, causing sliding of the disposal device on the underlying surface during the medical procedure. This tendency to slide on a surgical tray or table further increases the hazard for health workers handling the sharps, potentially causing deadly contamination of the health care worker.

Medical waste disposal devices also usually do not allow visual inspection and counting of the enclosed sharps or waste materials after the device is closed. In addition, the devices do not include in combination an accounting means to ensure the number and type of medical waste included in a closed and sealed container.

Current medical waste disposal typically requires large treatment systems which involve complex operation, and such systems are nonportable and highly expensive. Such systems include autoclaving, incineration and bulk chemical treatment of the medical waste.

It is, therefore, an object of the invention to provide an improved portable disinfecting and disposal device for medical waste.

It is another object of the invention to provide a novel method of on site disinfecting and disposal of medical waste prior to removal from the immediate area of the medical procedure.

It is a further object of the invention to provide an improved method and device for disposing of medical waste while rendering the waste biologically harmless at the immediate site of the medical procedures.

It is an additional object of the invention to provide a novel method and device for reliably sealing disinfected medical waste in a container.

It is still another object of the invention to provide an improved method and device for disposing of disinfected medical waste accounting for the number and type of medical waste in the disposal container after it is sealed.

It is still a further object of the invention to provide a novel medical waste disposal container which has a variety of convenient covers which contain the disinfectant and can be removed to release the disinfectant.

It is yet a further object of the invention to provide an improved medical waste disposal container having a cover for the disinfectant component constructed to seal in the disinfectant but is readily peeled in sections or as a whole cover from the container.

Other objects and advantages of the invention, together with the manner of use and operation, will become apparent from the Detailed Description hereinafter, from copending application having Ser. No. 07/836,629 incorporated by reference herein in its entirety and from the drawings described below:

BRIEF DESCRIPTION OF THE DRAWINGS

FIG. 1AA illustrates a top view of a bottom portion of a medical waste disposal device constructed in accordance with the invention and FIG. 1AB shows the top portion thereof; FIG. 1B shows a side elevation view of the assembled device of FIG. 1AA, FIG. 1CB is a front elevation view of the device view of FIG. 1AB; FIG. 1C illustrates a front elevation view of the device of FIG. 1A and FIG. 1D shows a cross section taken along 1D—1D in FIG. 1AB;

DETAILED DESCRIPTION OF PREFERRED EMBODIMENTS

Figure 2A:
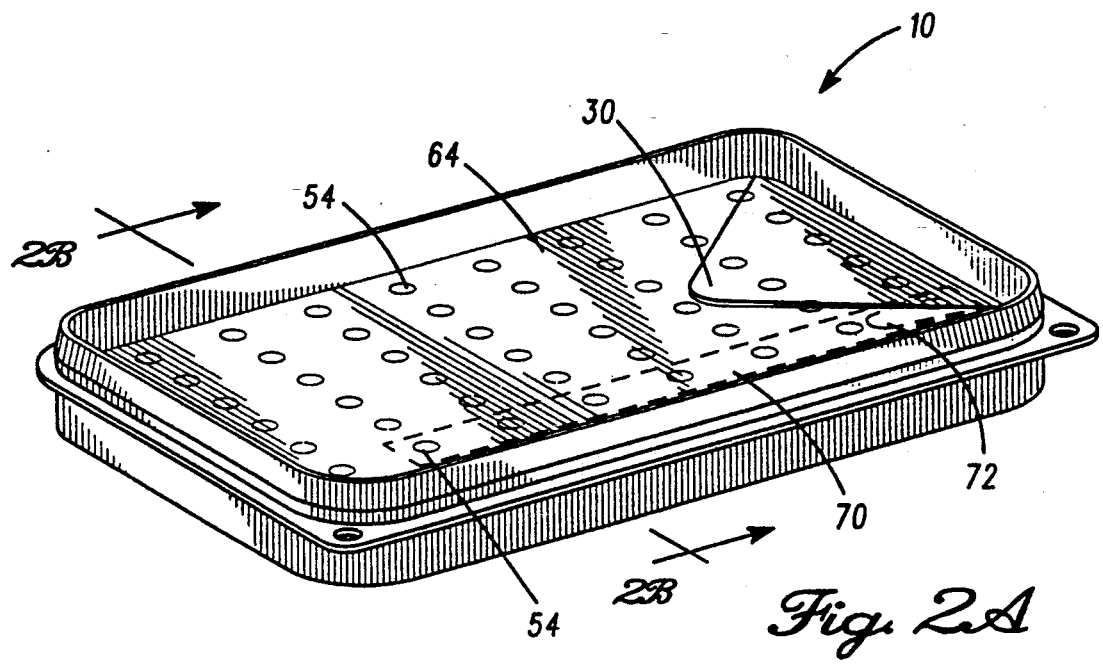
FIG. 2A shows a top portion of a disposal device with a peelable cover which can be removed in whole or by removal of more than one of a set of tear strips covering access openings to a disinfectant.

A medical disposal device constructed in accordance with the invention is indicated generally at 10 in FIG. 1. The medical disposal device 10 (hereinafter, "the device 10") is preferably a plastic material which is highly resistant to penetration under normal medical system use in order to prevent the sharps or other medical waste from penetrating the device 10, either from the inside or from an outside source. The plastic can be any available material and necessary thickness which will provide the desired penetration protection, such as polyvinyl chloride, polystyrene, polyethylene, polyethylene tetraphthalate ("PET"), polyethylene tetraphthalate glycol ("PETG") which can be Kodar copolyester 6763 (a trademark of Eastman Kodak), polypropylene, ethylene acrylic acid, Barex (a trademark of BP Chemicals, Inc.) and combinations thereof. The plastic also is preferably highly resistant to environmental effects or chemical attack, either from the medical waste and disinfectant inside the device 10 or from exterior chemical attack.

In a preferred form of the invention, the device 10 has a top portion 14 (see FIG. 1AA) and a separate bottom portion 16 (see FIG. 1AB). In other forms of the invention the top portion 14 and the bottom portion 16 can be coupled by connecting means, such as a hinge integrally coupling the top portion 14 to the bottom portion 16.

The bottom portion 16 includes means for securely attaching medical waste, which can include medical sharps (such as, surgical needles, scalpels and hypodermic needles), biological tissue and also other medical devices, such as sponges, tubing, bandages and cloth implements. The means for securely attaching medical waste can include, for example, peel-covered peelable adhesive areas 20, or other foam or fibrous areas 22 in FIG. 1A or contact cement and conventional viscous fluid media in area 23 which tightly hold an object which contacts the media. Depending on the type of medical waste, the adhesive areas 20 or the foam or fibrous areas 22 are preferred means for securely attaching the medical waste. For example, surgical needles 24 are easily secured in the foam or fibrous areas 22. The scalpel blades 26 can also be secured best by the foam areas 22.

The device 10 further includes in the top portion 14 a means for rendering harmless the medical waste, such as the surgical needles 24 attached to the foam areas 22. The means for rendering harmless is preferably a chemical to disinfect or sterilize the medical waste. The chemical could include, for example, a plastic packet 28 containing a commercial disinfectant or disinfectant soaked foam layer 29 or a liquid hospital-level disinfectant (45 in FIG. 2B) secured by a release mechanism as indicated in FIG. 1CB, 1D and 2B.

In FIG. 1D, the plastic packet 28 is covered with a peel layer 30. When the peel layer 30 is removed, the plastic packet 28 is ready for use. In this form of the invention the top portion 14 (See FIG. 1AB and 1D) can include coupled means such as spikes 31 (or 33 in the bottom portion 16 shown in FIG. 1AA) to penetrate the plastic packet 28 to release the disinfectant trapped beneath the sealed peel layer 30 (or to release disinfectant in the foam layer 29 in the top portion 14).

Figure 2B:
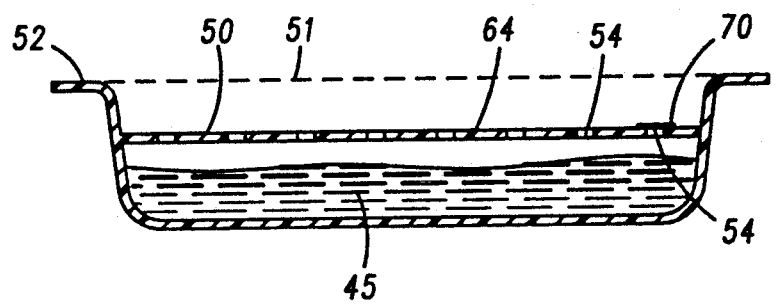
FIG. 2B is a cross section of the top portion in FIG. 2A taken along line 2B—2B in FIG. 2A.
Figure 3:
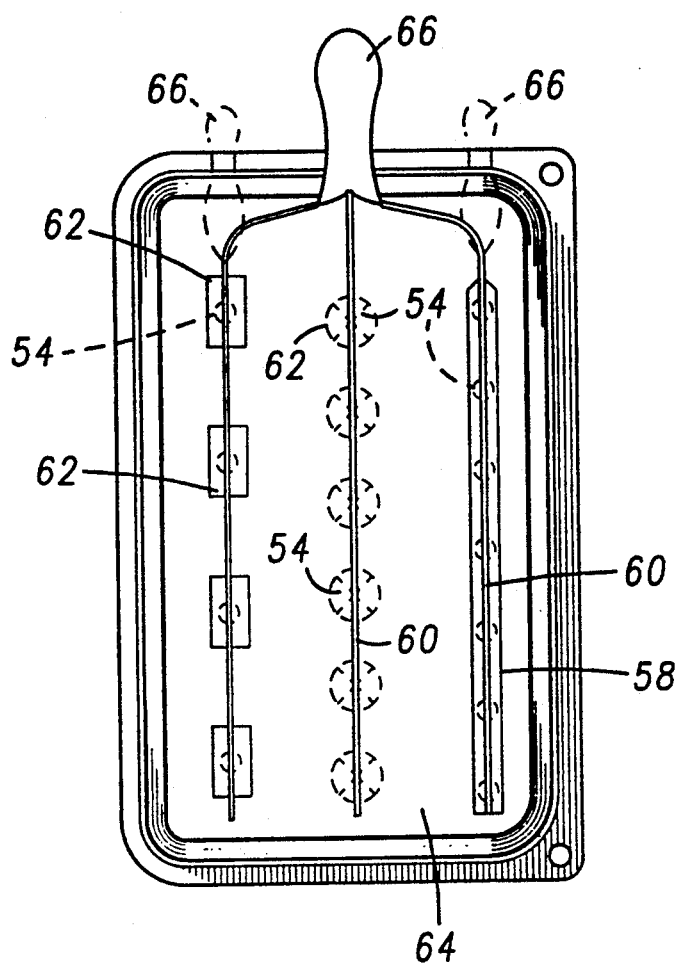
FIG. 3 illustrates a top view of a peelable plurality of tear strips over a variety of disinfectant access openings.

Alternative forms of the peel layer 30 are shown in FIGS. 2 and 3. In FIG. 2B is shown a cover element 50 or 51 (in phantom) sealingly coupled at perimeter 52.

Figure 4:
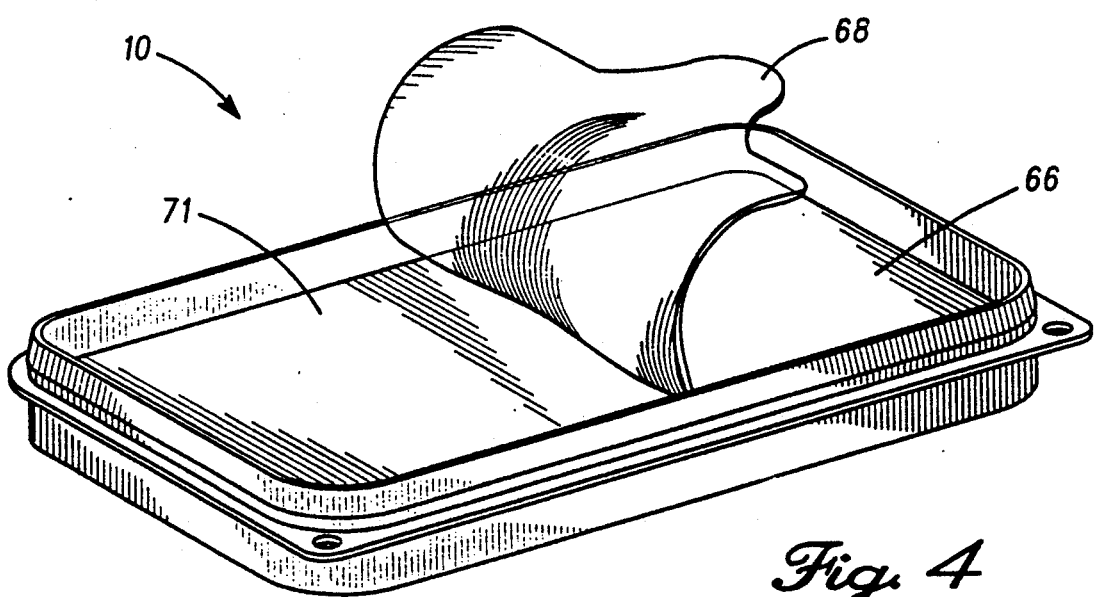
FIG. 4 shows a top view of a peelable cover over a membrane allowing controlled disinfectant release.

The cover elements 50 (or 51 in phantom) can be made, for example, of a soft or hard plastic of the top portion 14. The cover element 50 includes openings 54 (holes of slits, e.g.) which can be opened to release the disinfectant 45 in FIG. 2B (note there is not a plastic packet 28 in FIG. 2A and B as in the embodiment of FIG. 1). As shown in FIG. 3, as well as 2A, these openings 54 can be exposed by removing a peelable cover 64 having tear tabs 66 in one whole piece, or in part by tear strips 58 (in phantom) which are attached to strings 60 or other fibrous means. Hole cover seals 62 can also be attached to the strings 60 as shown in FIG. 3. Alternatively, as shown in FIG. 2A, the openings 54 can be exposed by tear strip top 64 removable by the tear tab 66. Another embodiment is also shown in phantom in FIG. 2A in the form of a thin tear strip 70 having pull tab 72. A further embodiment is shown in FIG. 4 wherein a plastic film or cover 66 is removable by pulling on tab 68 integrally coupled to the cover 66. In the embodiment of FIG. 4 there is also included a membrane cover 70 which allows controlled percolation release of the disinfectant disposed below the membrane cover 70 and which contacts the sharps or medical waste attached to the bottom portion 16 of the device 10.

In a most preferred embodiment the means for attaching medical waste is constructed of a material which allows percolation of a liquid or gaseous disinfectant through the attaching means. The disinfectant is therefore able to contact the attached medical waste and neutralize the biological contaminants associated with the medical waste.

When the user has disposed of the medical waste in the device 10 in the manner described above, a seal means is utilized in order to sealingly close the device 10. In particular, the seal means preferably acts to close the device 10 to prevent reopening the closed device 10. As shown in FIG. 1AA and FIG. 1AB a preferred embodiment comprises a recessed channel 29 on the bottom portion 16 and a protruding ridge 31 on the top portion 14. The recessed channel 56 matingly receives the protruding ridge 57, and the shapes of the channel 56 and ridge 57 are designed to sealingly close the device 10 and also for preventing nondestructive reopening of the device 10. The particular shape of the channel 56 and the ridge 57 can be, for example, a keyway design or other locking mechanism which allows easy entry of the ridge 31 into the channel 56 but preventing nondestructive removal of the ridge 31 from the channel 56.

In another form of the invention, the seal means can be, a first and second seal means, such as, conventionally peelable seal areas 32 and 34, respectively, shown in FIG. 1A. Other possible sealing means for the device 10 can be areas of contact cement, viscous fluid media, or thermally activated cement. In addition, the sealing means can be an epoxy formula wherein a viscous hardener portion is on the seal area of the top portion 14 and a viscous epoxy resin portion is on the seal area of the bottom portion 16.

Additional chemical means for rendering harmless the medical waste can include, for example, gaseous materials and acids which preferentially react with biological materials and/or disinfectants or sterilizing chemicals specific to selected viruses and/or bacteria. Once the device 10 is sealed and the chemical disinfection and/or sterilization is complete, the device 10 containing the decontaminated medical wastes can be more easily disposed of. An advantage of the device 10 is that the disposal standards are substantially more demanding and costly for disposal devices containing active harmful biological contaminants, compared to the deactivated contents in the device 10 of the invention.

The invention shown in FIG. 1A includes accounting means for numbering and identifying the medical waste contained in the device 10. There is shown a sequential numbering of each individual area 36, or alternatively, a grid system on each area, which retains one of the medical wastes. In other forms of the accounting means, different size areas can be used to attach medical waste. The actual numbering can be effectuated by numbers and/or grids imprinted on the housing of the device 10 as shown in FIG. 1A.

Another feature of the invention is the ability to firmly fix the position of the device 10 onto a holding table or other surface 40 shown in FIG. 1B. This can be accomplished using pincers 42 or gripping surface 44 coupled to the bottom of the bottom of the bottom portion 16. The pincers 42 are passed through the edge of the bottom portion 16 into surface 40.

Previous medical disposal systems suffer from a variety of problems. Rigorous health and environmental laws and regulations require extensive precautions be followed and expensive procedures implemented in order to dispose of biologically active medical waste. The instant invention overcomes a number of disadvantages of the prior art in a combination of a portable disposal device which reliably disinfects and retains the neutralized medical waste, while rendering harmless the medical waste at the local site of the medical procedures. The device also resists penetration of the housing and allows visual inspection of the sealed contents. The device 10 is also highly portable, combining the ability to reliably affix medical sharps and other such waste to the device, while simultaneously allowing disinfection of the medical sharps. In addition, the seal design avoids accidental opening or reuse. The resulting combination of features provides a simple, effective system which allows neutralizing of the biological contamination early in the waste disposal process. The system does not demand performance of expensive and unnecessary procedures. The system further allows accurate accounting for the specific medical wastes and thus ensures categorization as less hazardous waste. Many prior art systems allow unaccounted mixing of different types of medical waste and of unknown quantities. Such systems do not allow reliable classification as wastes of known types and number and therefore must be treated as the worst possible case.

While preferred embodiments of the invention have been shown and described, it will be clear to those skilled in the art that various changes and modifications can be made without departing from the invention in its broader aspects as set forth in the claims provided hereinafter

What is claimed is:

1. A portable disinfecting and disposal device for medical waste comprising:
   a plastic container for receiving medical waste and having a couplable top portion and bottom portion, said top portion including first seal means and said bottom portion including second seal means for sealing said top and bottom portions together;
   said bottom portion further including means for securely attaching said medical waste thereto; and
   said disinfecting and disposal device including a disinfectant contained therein for rendering harmless said medical waste attached to said bottom portion with said disinfectant sealed in said disinfecting and disposal device by a peelable cover unsealed by the user of said device and the user joining said first and second seal means to close said device, thereby sealing in and rendering harmless said medical waste at the local site of the medical procedure.

2. The disposal device as defined in claim 1 wherein said peelable cover comprises a tear strip.

3. The disposal device as defined in claim 2 wherein said tear strip comprises one unitary cover.

4. The disposal device as defined in claim 2 wherein said tear strip comprises a plurality of separately removable strips.

5. The disposal device as defined in claim 2 wherein each said tear strip includes a fibrous element coupled to said tear strip for removing said tear strip.

6. The disposal device as defined in claim 3 wherein said tear strip comprises a string coupled to an individual strip.

7. The disposal device as defined in claim 1 further including a cover element sealingly coupled to said top portion.

8. The disposal device as defined in claim 7 wherein said cover element includes access openings to the disinfectant.

9. The disposal device as defined in claim 8 wherein said peelable cover is disposed over said cover element and said peelable cover includes a plurality of individual seals covering said access openings to the disinfectant.

10. The disposal devices as defined in claim 8 wherein said peelable cover comprises a single layer.

11. The disposal device as defined in claim 8 wherein said peelable cover comprises a plurality of tear strips.

12. The disposable device as defined in claim 1 wherein said peelable cover comprises a layer with at least one pull tab.

13. The disposal device as defined in claim 7 wherein said cover element includes access openings of at least one of slits and open area holes.

14. The disposal device as defined in claim 12 further including a membrane element allowing controlled disinfectant release from said top portion.

15. A portable disinfecting and disposal device for medical sharps, comprising:
   a plastic container for receiving medical sharps and having atop portion and a bottom portion, said top portion including a first seal means along the entire perimeter thereof and said bottom portion including a second seal means for matingly sealing to said first seal means and said top and bottom portions joined by connecting means;
   said bottom portion further including means for securely attaching said medical sharps thereto;
   said device further including disinfectant for rendering harmless said medical sharps and said top portion attachable to said bottom portion with said disinfectant sealed into said device by a peelable cover of at least one tear strip removable by the user of said device and the user able to join said first and second seal means to close and prevent reopening of said device, thereby sealing in and rendering harmless said medical sharps; and
   identifying means for numbering and identifying said medical sharps coupled to said device.

16. The disposal device as defined in claim 15 further including a cover element sealingly engaged to said top portion and including access openings to said disinfectant.

17. The disposal device as defined in claim 16 wherein said access openings include at least one of slits and open hole areas.

18. The disposal device as defined in claim 15 wherein the plastic of said container is selected from the group consisting of polyethylene tetraphthalate, polyethylene tetraphthalate glycol, polyvinyl chloride, polystyrene, polyethylene, polypropylene, ethylene acrylic acid, Barex ® and combinations thereof.

19. The disposal device as defined in claim 15 further including a numbering and/or grid system imprinted on at least one of said top and said bottom portions.

* * * * *